US00PP13300P3

(12) United States Plant Patent
Olesen et al.

(10) Patent No.: US PP13,300 P3
(45) Date of Patent: Dec. 3, 2002

(54) HYBRID TEA ROSE PLANT NAMED 'POULJOSE'

(76) Inventors: L. Pernille Olesen, Hillerødvejen 49, DK-3480, Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/776,136

(22) Filed: Feb. 1, 2001

(65) Prior Publication Data

US 2002/0152516 P1 Oct. 17, 2002

(51) Int. Cl.[7] ..... A01H 5/00

(52) U.S. Cl. ..... Plt./133

(58) Field of Search ..... Plt./133, 130

*Primary Examiner*—Bruce R. Campell

*Assistant Examiner*—June Hwu

(57) ABSTRACT

A new Hybrid Tea rose which has abundant, creamy white flowers and attractive foliage. This new and distinct variety has shown to be uniform and stable in the resulting generations from asexual propagation.

1 Drawing Sheet

BOTANICAL CLASSIFICATION

*Rosa hybrida* 'POULjose'.

SUMMARY OF THE INVENTION

The present invention constitutes a new and distinct variety of garden rose plant which originated from a controlled crossing between 'Polarstern', an unpatented variety, and 'POULari', described and illustrated in U.S. Plant Pat. No. 9,274, issued on Sep. 5, 1994. The two parents were crossed during the summer of 1990 and the resulting seeds were planted in a controlled environment in Fredensborg, Denmark. The new variety is named 'POULjose'.

The new rose may be distinguished from its seed parent, 'Polarstern', by the following combination of characteristics:

1. 'POULjose' has fewer petals than 'Polarstern'.
2. 'POULjose' produces a greater quantity of flowers per stem than the seed parent.
3. 'POULjose' exhibits more anthocyanin than the seed parent.

The new variety may be distinguished from its pollen parent, 'POULari' by the following combination of characteristics:

1. 'POULjose' has fewer petals than 'POULari'.
2. The foliage of 'POULjose' is less glossy than the foliage of 'POULari'.

The objective of the hybridization of this rose variety was to create a new and distinct variety for garden use with unique qualities, such as:

1. Uniform and abundant flowers;
2. Vigorous, but compact growth when propagated both as a budded rose and on its own roots;
3. Disease resistance.

This combination of qualities is not present in previously available commercial cultivars of this type and distinguish 'POULjose' from all other varieties of which we are aware.

As part of their rose development program, L. Pernille Olesen and Mogens N. Olesen germinated the seeds from the aforementioned hybridization during the winter of 1990 and conducted evaluations on the resulting seedlings in a controlled environment in Fredensborg, Denmark.

'POULjose' was selected in the spring 1991 by the inventors as a single plant from the progeny of the aforementioned hybridization. Asexual reproduction of 'POULjose' by traditional budding and rooted cuttings was first done by L. Pernille and Mogens N. Olesen in their nursery in Fredensborg, Denmark in summer 1991. This initial and other subsequent asexual propagations conducted in controlled environments have demonstrated that the characteristics of 'POULjose' are true to type and are transmitted from one generation to the next.

BRIEF DESCRIPTION OF THE DRAWING

The accompanying color illustration shows as true as is reasonably possible to obtain in color photographs of this type the variety rose 'POULjose'. Specifically illustrated in SHEET 1 are 'POULjose's' foliage, flower buds, partially opened buds, and an open bloom.

DETAILED DESCRIPTION OF THE VARIETY

The following is a description of 'POULjose', as observed in its growth in a nursery in Jackson County, Oreg., on plants aged sixteen weeks. Color references are made using The Royal Horticultural Society (London, England) Colour Chart, 1995, except where common terms of color are used.

For a comparison, several physical characteristics of the rose variety 'POULari', a rose variety from the same inventors described and illustrated in U.S. Plant Pat. No. 9,274 and issued on Sep. 5, 1994 are compared to 'POULjose' in Chart 1.

CHART 1

| | 'POULjose' | 'POULari' |
|---|---|---|
| Color of open flower, outer petals, middle zone. | White Group 155B | White Group 155D to 157D |
| Petalage | 25–30 | 55–75 |
| Upon opening color basal petal spot, outer side | Yellow Group 7D | Greyed-Yellow Group 160D |

Classification:
*Commercial.*—Hybrid tea.
Parents:
*Seed parent.*—'Polarstern'.
*Pollen parent.*—'POULari'.

FLOWER AND FLOWER BUD

Blooming habit: Recurrent.
Flower bud:
*Bud color.*—As sepals unfold, bud color is Yellow Group 4D. At ¼ opening, bud color is White Group 155D.
*Bud form.*—Ovate.
*Sepals.*—Size: 8 mm (w)×11 mm (l) Color, upper surface: Yellow-Green Group 144A. Lower surface: Weak foliaceous appendages on three of the five sepals. Color, lower surface: Green Group 138B. Texture, upper surface: Slightly pubescent. Stipitate glands present on sepal margins. Texture, lower surface: Slightly pubescent.
*Receptacle.*—Size: 5 mm (l)×8 mm (h).
*Peduncle.*—Surface: Moderate abundance of hairs and prickles. Color: Yellow-Green Group 144A. Strength: Strong. Length: 40 to 50 mm average length.
*Borne.*—Singularly.
Flower bloom:
*Fragrance.*—Weak.
*Size.*—Medium to large. Average flower diameter is 90 mm when open.
*Form.*—Shape of flower when viewed from the side: Upper part: Flat. Lower part: Flat. Viewed from above: Irregularly rounded.
*Petalage.*—Double. Average range: 25–30 petals under normal conditions.
*Duration.*—Flowers last from 6 to 10 days. The bloom is self-cleaning.
Color:
*Petals, open bloom.*—Inner Side: Middle zone: White Group 155B. Marginal zone: White Group 155B. Basal petal spot: Yellow Group 7D. Outer side: Middle zone: White Group 155B. Marginal zone: White Group 155B. Basal petal spot: Yellow Group 7D.
*General tonality.*—On open flower White Group 155A.
Petals:
*Petal reflex.*—Weak.
*Undulation of margin.*—Weak.
*Petal size.*—35 mm (l)×30 mm (w).
*Petal shape.*—Deltoid. Margin is entire.
*Surface texture.*—Smooth.
*Petaloids.*—5 to 8 petaloids. Petaloids are, on average, 15 mm long and 10 mm wide. Coloration on both upper and lower surfaces of petaloids is White Group 155A.

Reproductive organs:
*Pollen.*—Color: Yellow-Orange Group 17A. Quantity: Average.
*Anthers.*—Size: 4 mm long. Color: Yellow Group 1D. Quantity: Approximately 20–25.
*Filaments.*—Color: Yellow-Green Group 145C and D. Length: 10 mm.
*Stigmas.*—Slightly superior in location to anthers. Color: Greyed-White Group 157A.
*Styles.*—Color: Greyed-White Group 157B.
*Seed formation.*—Hips: Not observed.
*Pistils.*—Length: 20 mm long. Quantity: 25–30.

PLANT

Plant growth: Upright to bushy. When grown as a budded field grown plant on *Rosa multiflora* understock, the average height of the plant is 60–80 cm and the average width is 50 cm.
Stems:
*Thorns.*—Incidence: None on upper half of stems; lower portion of stems, 4 thorns per 10 cm of stem. Size: Average length is 8 mm. Shape: Linear. Color: Yellow-Green Group 146C.
*Surface texture.*—Young wood: Smooth. Older wood: Rough.
Plant foliage:
*Leaf size.*—40 mm (l)×30 mm (w).
*Glossiness.*—Medium glossiness.
*Color.*—Upper Leaf Surface: Green Group 137A. Lower Leaf Surface: Green Group 128B. Juvenile foliage: Upper Leaf Surface: Yellow-Green Group 144A. Lower Leaf Surface: Green Group 128B. Anthocyanin intonation: Present on upper and lower surface leaflet margins, sepal tips, peduncles, and petioles. Color: On juvenile foliage, Greyed-Red Group 181B.
Plant leaflets:
*Leaflet.*—Cross Section: Slightly concave. Margin Undulation: Weak to medium. Thickness: Moderately thick. Size: 13 mm (l)×10 mm (w). Venation: Reticulate. Edge: Serrated. Apex: Cirrose. Base: Rounded.
*Stipules.*—Size: 7 mm (w)×23 mm (l). Color: Yellow-Green Group 144B. On plants grown under high light conditions, peduncle may exhibit intonations of Greyed-Red Group 181A. Stipitate glands: Present on edges of stipules. Anthocyanin: Greyed-Red Group 181A.
*Petiole.*—Length: 10 mm. Color: Yellow-Green Group 144C. Underneath: Yellow-Green 144A. Margins: Yellow-Green Group 144A. Anthocyanin: None noted.
*Rachis.*—Color: Yellow-Green Group 144C. Underneath: Yellow-Green 144A; one thorn present. Margins: Yellow-Green Group 144A.
*Terminal leaflet.*—Size: 14 mm (l)×11 mm (w). Shape: Rounded.
Disease resistance: Above average resistance to mildew, rust, black spot, and Botrytis under normal growing conditions in Hannover, Germany and Fredensborg, Denmark.
Cold hardiness: The variety 'POULjose' has been found to be cold hardy in Fredensborg, Denmark and Hannover, Germany.

Cold hardiness: The variety 'POULjose' has been found to be resistant to damage from cold, heat and drought damage in USDA Zone 7.

We claim:

1. A new and distinct variety of rose plant of the Hybrid Tea rose class, substantially as herein illustrated and described as a distinct and novel rose variety due to its abundant creamy white flowers, disease resistance, and extended period of bloom.

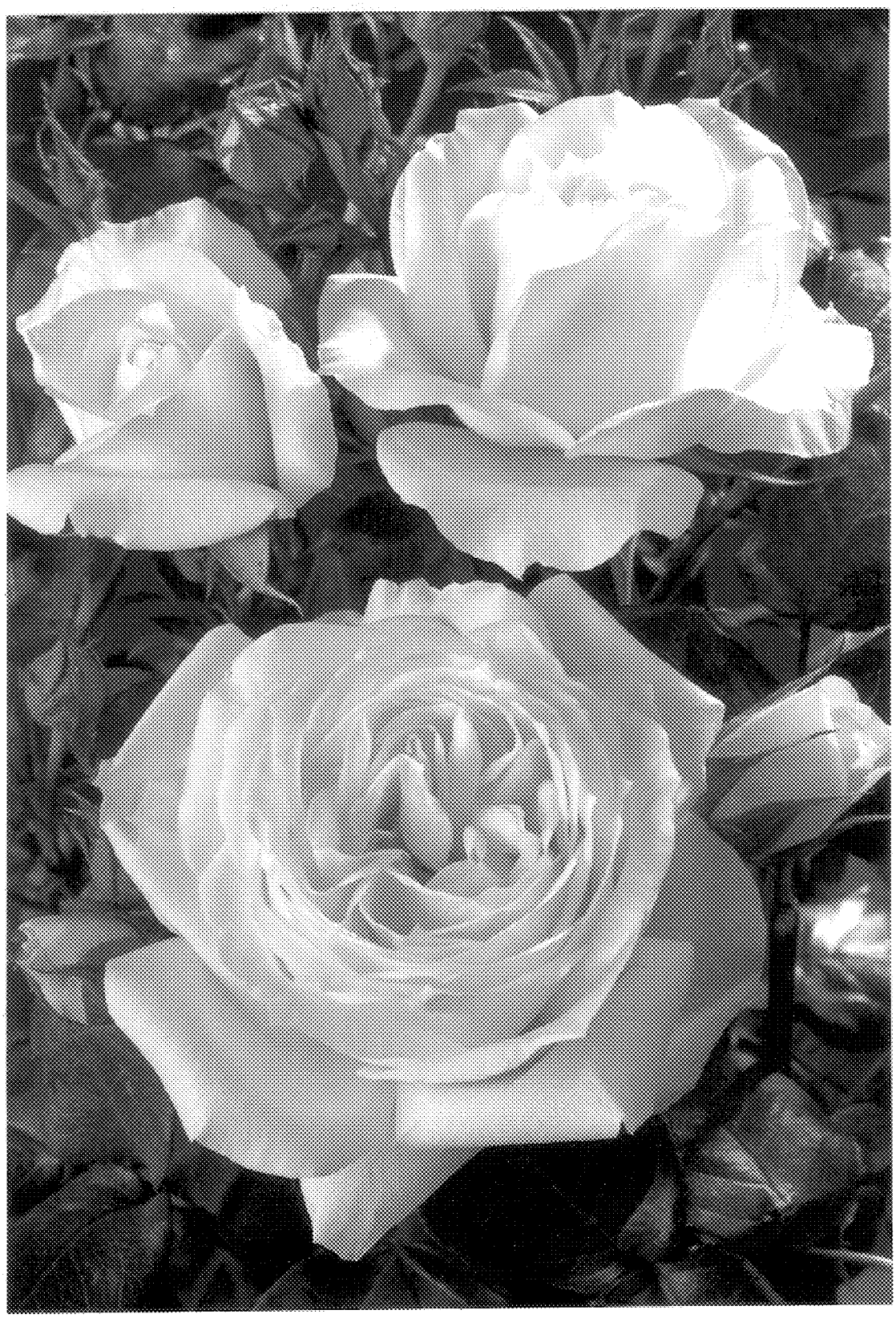

* * * * *